United States Patent [19]

Cutter

[11] 4,319,581
[45] Mar. 16, 1982

[54] HEART PULSE MONITORING APPARATUS

[76] Inventor: John W. Cutter, 10 Sleepy Hollow La., Orinda, Calif. 94563

[21] Appl. No.: 161,074

[22] Filed: Jun. 19, 1980

[51] Int. Cl.³ .............................................. A61B 5/04
[52] U.S. Cl. .................................... 128/707; 128/639
[58] Field of Search ........................ 128/690, 706–707, 128/639; 272/73; 74/551.8–551.9

[56] References Cited

U.S. PATENT DOCUMENTS

| | | | |
|---|---|---|---|
| 3,702,113 | 11/1972 | Blockley | 128/707 |
| 3,908,640 | 9/1975 | Page | 128/689 |
| 4,112,928 | 9/1978 | Putsch | 128/707 |

OTHER PUBLICATIONS

"Instapulse" Sales Brochure, Biosig. Inc., 5471 Royalmount Ave., Montreal, Canada H4P1J3, 9/78.

Primary Examiner—Robert W. Michell
Assistant Examiner—Francis J. Jaworski
Attorney, Agent, or Firm—Claude A. S. Hamrick

[57] ABSTRACT

Heart pulse rate is measured by use of a pair of handle grips (12), (14) for a bicycle handle (16), and the like, one of which grips (12) provides a conductive contact (22), (23) between one of the hands of a user of the apparatus and an associated end of the handlebar. The other of the hand grips (14) includes a pair of contacts (32), (34) arranged for being simultaneously engaged by the other hand of the user of the device, with a further contact (30) being disposed for electrical connection to an end of the handlebar associated with the other of the hand grips. In this manner, the handlebar serves to complete a circuit through the user's body and enables a pulse monitoring apparatus (26) preferably provided on one of the hand grips (14) to detect and display the pulse rate of the user of the apparatus.

10 Claims, 4 Drawing Figures

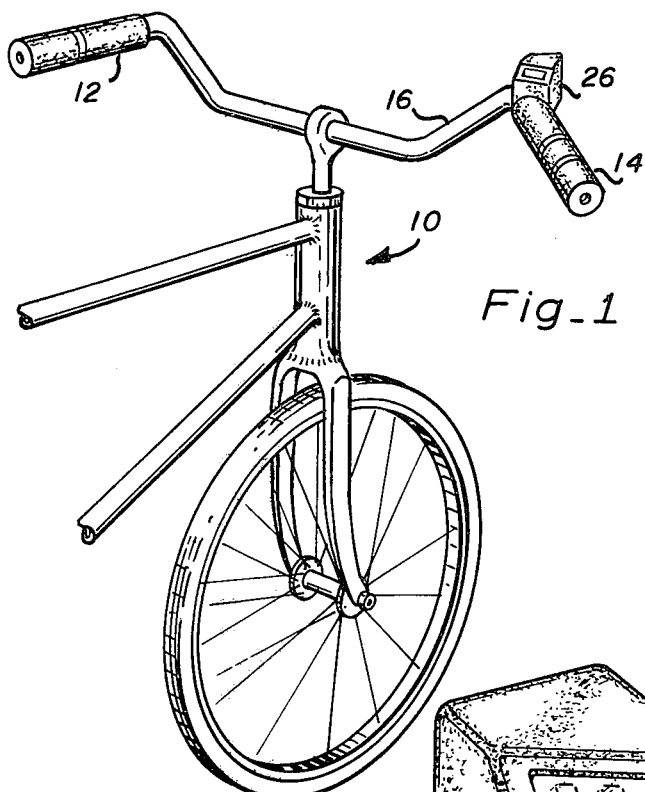
Fig_1
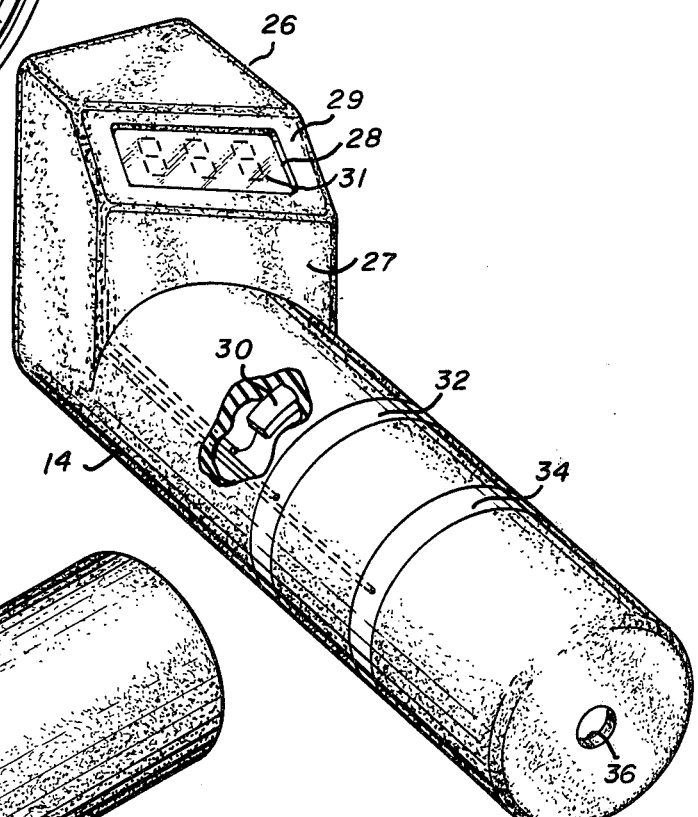
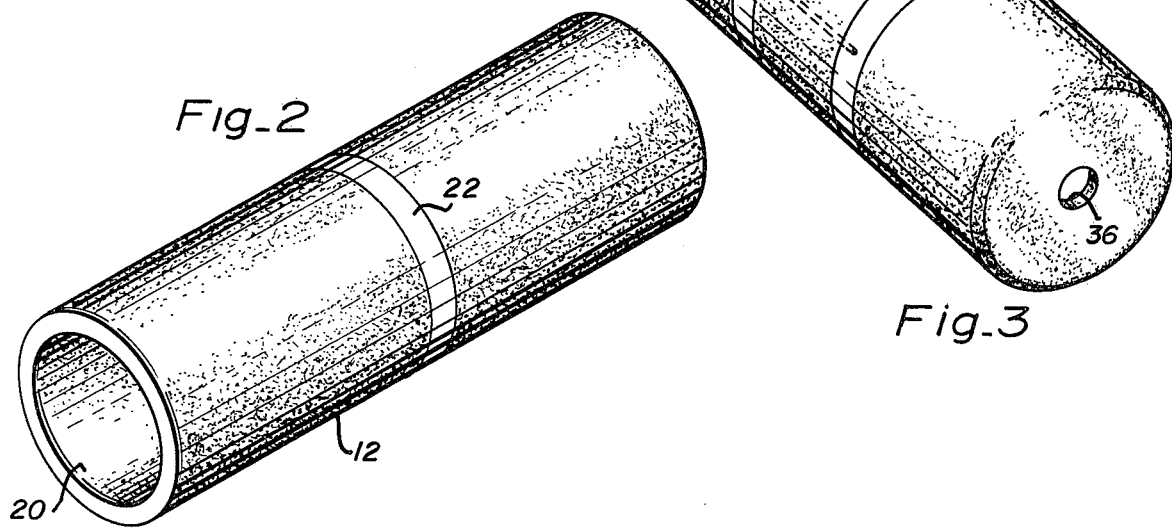
Fig_2
Fig_3

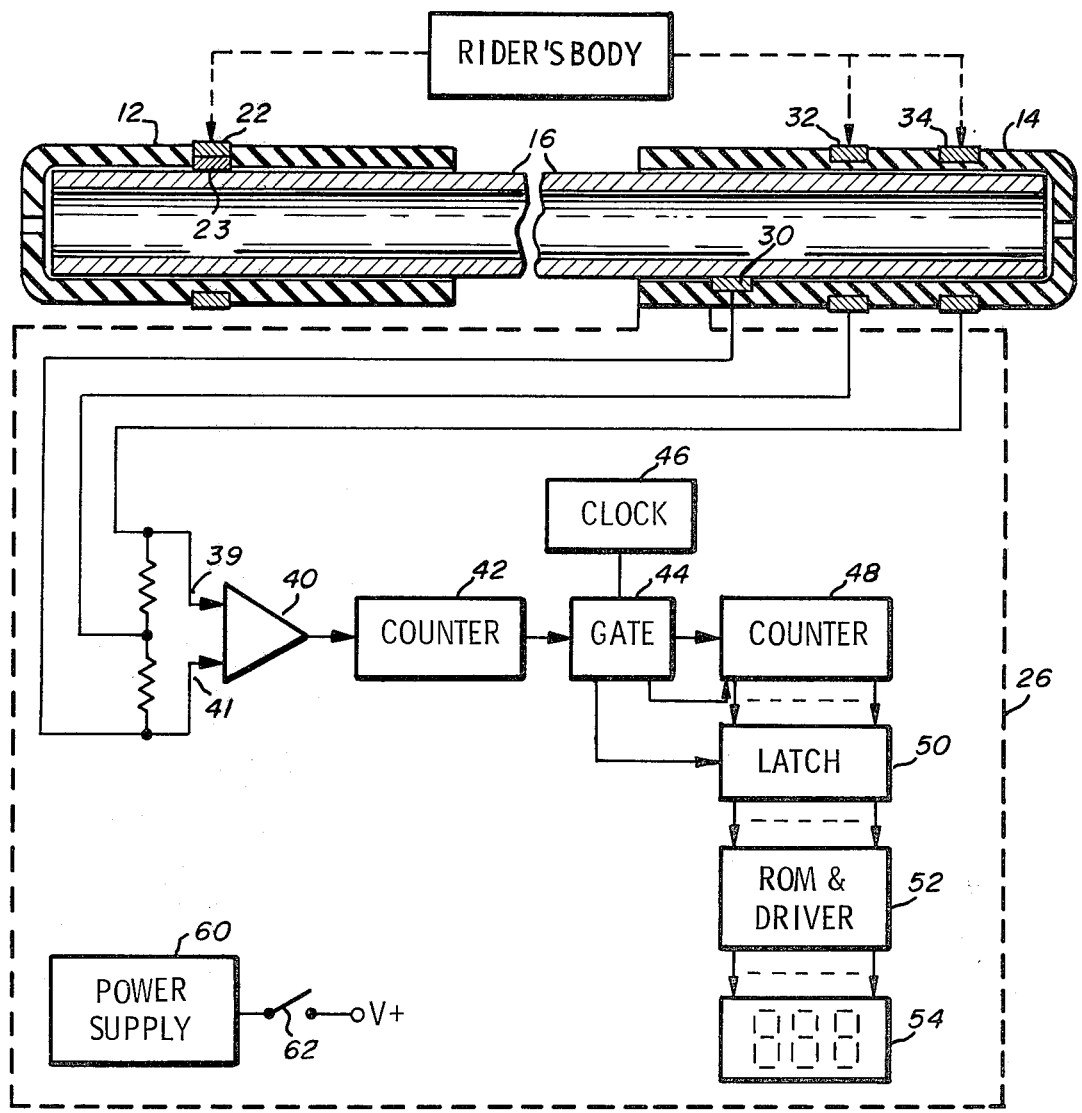
Fig_4

HEART PULSE MONITORING APPARATUS

BACKGROUND OF THE INVENTION

1. Field of the Invention

The present invention relates generally to physiological monitoring apparatus and more particularly, to a device for attachment to an ordinary bicycle to indicate to the user his heart pulse rate.

1. Description of the Prior Art

For health conscious persons who bicycle or use stationary exercise devices, which have handlebars that are gripped while the device is in use, it is sometimes desirous to know the heart pulse rate of the user. Devices for providing such information have been provided in the past but typically require that the user attach electrodes to his body or wear special sensors on his fingers, ear lobes or other appendages. This of course adds inconvenience to the use of such equipment and in some cases interferes with the actual use and enjoyment of the exercise device.

SUMMARY OF THE INVENTION

It is therefore a principle object of the present invention to provide a means which when attached to a bicycle is capable of measuring the heart pulse rate of the user without requiring application of special electrodes or body attachment probes.

Another object of the present invention is to provide a heart pulse monitoring apparatus for bicycles which can be easily attached to the bicycle without requiring modification thereof.

Still another object of the present invention is to incorporate a heart pulse monitoring apparatus into handlebar grips of ordinary configuration which when gripped by the user provide the necessary bodily contact required to enable monitoring electronics to perform their function.

Briefly, a preferred embodiment of the present invention includes a pair of handle grips for a bicycle, one of which provides a conductive contact between one of the user's hands and one end of the handlebar, and the other of which includes an electronic monitor and digital display along with a pair of contacts for simultaneously contacting the other hand of the user and a further contact for connection to the other end of the handlebar. The handlebar serves as a means for completing a circuit through the user's body and enables the pulse monitoring apparatus to detect and display his pulse rate.

An advantage of the present invention is that it can be attached directly to the handlebars of either an ordinary bicycle or an exercycle without modification.

Another advantage of the present invention is that it is entirely self-contained in the handlebar grip devices and requires no external leads or probe connections.

These and other objects and advantages of the present invention will no doubt become apparent to those of ordinary skill in the art after having read the following detailed description of a preferred embodiment which is illustrated in the several figures of the drawing.

IN THE DRAWING

FIG. 1 is a perspective view illustrating the front portion of a bicycle having heart pulse monitoring apparatus in accordance with the present invention installed thereon;

FIG. 2 is a perspective view illustrating the left side handle grip shown in FIG. 1;

FIG. 3 is a perspective view further illustrating the right side handle grip and digital display shown in FIG. 1 of the drawing; and FIG. 4 is a diagram schematically illustrating the operative components of heart pulse monitoring apparatus in accordance with the present invention.

DETAILED DESCRIPTION OF THE PREFERRED EMBODIMENT

In FIG. 1 of the drawing, the front portion of a bicycle 10 is illustrated having a pair of hand grips 12 and 14 mounted to a metal handlebar 16 in accordance with the present invention. These hand grips slide directly over the ends of the handlebar 16 and include means for making direct electrical contact to each end thereof. Handlebar 16 must be continuous and made of electrically conducting material, otherwise a separate conductor would have to be either affixed to the surface thereof or be threaded through the handlebar itself.

Referring now to FIGS. 2 and 3, the actual configuration of the hand grips 12 and 14 are illustrated more clearly. As depicted in FIG. 2, the grip 12 is shown reversed end-for-end as compared to its configuration in FIG. 1 so as to illustrate that the end 20 is open for receiving the left end of handlebar 16. Located approximately midway down the grip is a metallic ring 22 which circumscribes the grip and includes portions 23 which extend through the grip to make good ohmic contact with the end of handlebar 16 when installed thereon.

The position of ring 22 on the hand grip is selected so as to insure that it is contacted by the user's hand when the bicycle is in operation. Alternatively, the entire grip could be made of conductive rubber or plastic or could have one or more portions thereof made of such material so long as good ohmic contact is made from the user's hand to the handlebar via the conductive grip component.

In FIG. 3, an enlarged version of the right hand grip 14 is shown and includes a portion forming a housing 26 for containing heart monitoring electronic circuitry and batteries for powering the device. The lower front wall 27 of housing 26 is angled relative to the longitudinal axis of the hand grip portion and the upper front wall portion 29 is sloped rearwardly to provide a better viewing angle for the window 28 through which a suitable LCD, LED or other indicating display 31 may be viewed. Alternatively, the display 31 could be in the form of a dial, pointer, combination of lights, etc.

Grip 14 also includes an internally disposed handle bar contacting ring 30 and two external, hand contacting rings 32 and 34. Ring 30 is insulated from the outside of the grip by means of the grip body and is intended to provide ohmic contact with the right end of handlebar 16 to thereby receive the ECG signal from contact 32. The rings 32 and 34 are insulated from the handlebar by means of the grip body and are intended to provide good ohmic contact with the user's hand. Each of the rings 30, 32 and 34 is coupled to the electronics contained within the housing 26 by means of insulated conductors 35 formed in the grip body.

The grip 14 and housing portion 26 are preferably a unitary molded part having the rings 30, 32 and 34 either molded in situ or positioned within grooves formed in the grip body during its fabrication. The electronic circuitry contained within housing 26 is of course added following the molding of the grip unit per se. As is standard for most hand grips, a vent opening 36 is provided in the end of each handle so as to vent air trapped within the handle and/or grip thus allowing the grips to be more easily installed.

Although the rings 30, 32 and 34 are shown as continuous metallic rings they could also be made of metallic pads, longitudinal strips or of other configurations of either metal, conductive rubber or plastic material, the important features being that contact 30 electrically engage handlebar 16 and not be engageable by the user's hand, while contacts 32 and 34 must make good ohmic contact with the user's hand and be electrically insulated from handlebar 16.

Turning now to FIG. 4 of the drawing, a partially broken longitudinal cross section of the hand grip 12, handlebar 16 and hand grip 14 is illustrated along with a block diagram schematically showing the functional components of the heart pulse monitor contained within housing 26, the latter being represented by the dashed lines.

As illustrated, the handle 12 is a sleeve of insulating material which is merely slipped over the end of handlebar 16 such that one or more contact projections 23 of its contact ring 22 ohmically engage the conductive surface of handlebar 16. As previously indicated, the contact ring 22 could take many alternative forms and could even consist of whole or a portion of grip 12 being fabricated of conductive rubber or the like.

Grip 14 is an insulating body which likewise slips over an end of handlebar 16. In being so positioned, the internal contact ring 30 engages the conductive surface of bar 16. Note that ring 30 is disposed in an annular groove on the inside surface of grip 14 and is insulated by the grip body from the rider's hand. The rings 32 and 34 are electrically isolated from handlebar 16 by means of grip body 14 but are positioned so that each readily engages the hand of the rider when he grasps the grip. As also indicated above, any other suitable form of electrical contact mechanism could be used in place of the rings 30, 32 and 34.

Contained within the dashed lines 28 is an electronic monitoring circuit including an amplifier 40, a first counter 42, a gate 44, a clock 46, a second counter 48, a latch 50, a read only memory (ROM) and driver 52 and a 3 digit LED or LCD display unit 54. By means of the circuit completed from contact 30 through handlebar 16, contact 22 and through the rider's body to contacts 32 and 34, amplifier 40, which is coupled to contact rings 30, 32 and 34, will detect the R-waves generated by the rider's body. Amplifier 40 will then generate an electric pulse for every detected R-wave pulse and each such pulse will be input to counter 42 which will in turn generate an output signal each time a predetermined number of R-wave pulses are counted. Each output of counter 42 actuates gate 44 reset counter 48 and to input a stream of clock pulses from clock 46 into counter 48 during the interim between successive gate actuations. Gate 44 also actuates a latch at the end of each of said predetermined number of R-wave pulses so as to store the last count contained in counter 48. The data stored in latch 50 is then input to the ROM and indicator driver unit 52 which converts each end count of counter 48 into a signal suitable for causing indicator 54 to display a number indicative of the average heart pulse rate which occurred during the count period determined by counter 42.

Although it would be possible to display the heart rate as determined between each consecutive R-wave pulse, this would not be practical because it is well known that the intervals between successive heart pulses fluctuate materially and consequently provide little useful information. A much more meaningful measure of pulse rate is obtained by averaging the rate over a suitable plurality of heart pulses. Accordingly, in the preferred embodiment, the first counter 42 counts the pulses output from amplifier 40 and upon the count of a predetermined number of heart pulses, such as 8, for example, causes counter 48 to count clock pulses continuously over each 8 R-wave pulse duration before the result is stored in latch 50. ROM 52 is thus programmed to convert the count contained in latch 50 into a digital output corresponding to the average clock count over the 8 pulse duration and such output will cause a number to be displayed by unit 52 which represents the rider's pulse rate.

Also contained within the housing 26 is a suitable power supply 60 for providing operative power to the various components of the circuit. A simple external manual switch 62 is provided for turning on the monitoring circuit. However, it will also be appreciated that the manual switch could be eliminated and means could be substituted therefor which would sense the presence of the rider's hands on the hand grips and then automatically supply power to the circuit.

In operation, once the switch 62 is closed, the device will be ready to count the R-wave pulses of the rider.

As will be readily understood by those skilled in the art, the R-wave voltages generated by the rider's body will be applied across the input terminals 39 and 41 of amplifier 40 causing it to generate a series of R-wave pulses which will be counted by counter 42 and used to actuate gate 44 and input pulses from the 1 Kz clock 46 into counter 44. Counter 44 will then continue to count during the next eight R-wave pulses, at the conclusion of which the count in counter 48 will be output to latch 50 and counter 48 will be reset to begin another count sequence. Latch 50 will then input its contents to ROM 50 which will in turn output signals for driving the digital display 52.

Although the present invention has been described in terms of a simplified preferred embodiment, it will be appreciated that numerous alterations and modifications of the invention may become apparent to those skilled in the art. It is therefor intended that the following claims be interpreted as covering all such alterations and modifications as fall within the true spirit and scope of the invention.

What is claimed is:

1. A heart pulse monitoring apparatus for attachment to the handlebar of an exercising device for measurement of the pulse rate of a user, comprising:
   a first hand grip for attachment to one end of the handlebar of a bicycle or stationary exercise device and having first means for completing an electrical circuit from a hand of said user when gripping said first hand grip to a conductive part of said handlebar;
   a second hand grip including a second means for electrically contacting the other end of said handlebar, said second means being electrically isolated from the other hand of said user when gripping said second hand grip, third and fourth means disposed upon said second hand grip in spaced apart relationship and adapted to electrically engage said other hand of said user when gripping said second hand grip; and signal monitoring means electrically coupled to said second, third and fourth means for measuring electric pulses created in the body of said user whose hands are holding said first and second hand grips and for indicating the heart pulse rate of such body.

2. A heart pulse monitoring apparatus as recited in claim 1 wherein said third and fourth means are spaced apart metallic bands circumscribing the external surface of said second hand grip.

3. A heart pulse monitoring apparatus as recited in claim 1 wherein said second hand grip includes means forming a housing for containing said signal monitoring means.

4. A heart pulse monitoring apparatus as recited in claim 3 wherein said signal monitoring means includes a digital display indicator and said housing includes a window formed therein through which said indicator may be viewed.

5. A heart pulse monitoring apparatus as recited in claims 1, 2, 3 or 4 wherein said signal monitoring means includes means for detecting the R-waves generated by the body whose hands are holding said first and second hand grips and for generating electrical pulses corresponding thereto.

6. A heart pulse monitoring apparatus as recited in claim 5 wherein said signal monitoring means further includes means for determining the number of said electrical pulses generated per a predetermined unit of time and for generating a rate signal corresponding thereto.

7. A heart pulse monitoring apparatus as recited in claim 6 wherein said signal monitoring means further includes a signal conversion means for converting said rate signal into an electrical signal suitable for driving an indicator.

8. A heart pulse monitoring apparatus as recited in claim 6 wherein said means for determining includes a clock for generating clock pulses, a counter, and a gate responsive to said electrical pulses and operative to enable said counter to count the number of clock pulses occurring between a predetermined number of said electrical pulses and develop said rate signal.

9. A heart pulse monitoring apparatus as recited in claim 8 wherein said signal monitoring means further includes a signal conversion means for converting said rate signal into an electrical signal suitable for driving an indicator.

10. A heart pulse monitoring apparatus as recited in claim 9 wherein said signal monitoring means further includes a self-contained power supply.

* * * * *